(12) United States Patent
Robins et al.

(10) Patent No.: US 7,572,909 B2
(45) Date of Patent: Aug. 11, 2009

(54) METHOD FOR THE PREPARATION OF 2-HALO-2'-DEOXYADENOSINE COMPOUNDS FROM 2'-DEOXYGUANOSINE

(75) Inventors: Morris J. Robins, Provo, UT (US); Zlatko Janeba, Los Angeles, CA (US); Paula Francom, Salt Lake City, UT (US)

(73) Assignee: Brigham Young University, Provo, UT (US)

( * ) Notice: Subject to any disclaimer, the term of this patent is extended or adjusted under 35 U.S.C. 154(b) by 0 days.

(21) Appl. No.: 10/529,106

(22) PCT Filed: Sep. 25, 2003

(86) PCT No.: PCT/US03/30386

§ 371 (c)(1),
(2), (4) Date: Oct. 9, 2006

(87) PCT Pub. No.: WO2004/028462

PCT Pub. Date: Apr. 8, 2004

(65) Prior Publication Data

US 2007/0032645 A1    Feb. 8, 2007

Related U.S. Application Data

(60) Provisional application No. 60/416,329, filed on Oct. 4, 2002, provisional application No. 60/413,915, filed on Sep. 25, 2002.

(51) Int. Cl.
   *C07H 19/173*    (2006.01)
(52) U.S. Cl. ..................... 536/27.7; 536/27.81
(58) Field of Classification Search ............... 536/27.7
   See application file for complete search history.

(56) References Cited

U.S. PATENT DOCUMENTS

| | | | | |
|---|---|---|---|---|
| 5,208,327 | A | * | 5/1993 | Chen ..................... 536/27.7 |
| 5,446,139 | A | | 8/1995 | Seela et al. |
| 5,668,270 | A | * | 9/1997 | Bauman et al. ......... 536/26.71 |
| 6,252,061 | B1 | | 6/2001 | Sampath et al. |
| 6,541,626 | B2 | | 4/2003 | Sanghvi et al. |
| 6,596,858 | B2 | | 7/2003 | Sampath et al. |

FOREIGN PATENT DOCUMENTS

WO    WO 2004/028462 A2    4/2004

OTHER PUBLICATIONS

Francom et al. J. Org. Chem. 2002, 67, p. 6788-6796, available online on Aug. 29, 2002.*
Doraiswamy L.K. Organic Synthesis Engineering, 2001, Oxford University Press, p. 3-13.*
Lin et al. Organic Letters, 2000, 2(22), p. 3497-3499.*

Bridson, Peter K., et al., "Acylation of 2',3',5'-Tri-*O*-acetylguanosine," 21 *J. Chem. Soc., Chem. Commun.* 791-792 (1977).
Bridson, Peter K., et al., "Conversion of Guanosine into its $N^2$-Methyl Derivative," 1 *J. Chem. Soc., Chem. Commun.* 447-448 (1977).
Daskalov, Hristo Petrov, et al., "New Guanosine Derivatives: Facile $O^6$-Phosphorylation, Thiophosphinylation Sulfonylation and Silylation of Guanosine Derivatives by 4-Dimethylaminopyridine Catalized Reaction," 21 (33) *Tetrahedron Lett.* 3899-3902 (1980).
Francom, Paula, et al., "Nucleic Acid Related Compounds. 116. Nonaqueous Diazotization of Aminopurine Nucleosides. Mechanistic Considerations and Efficient Procedures with *tert*-Butyl Nitrite or Sodium Nitrite," 67(19) *J. Org. Chem.* 6788-6796 (2002).
Gaffney, B.L. and R.A. Jones, "Synthesis of O-6-Alkylated Deoxyguanosine Nucleosides," 23(22) *Tetrahedron Lett.* 2253-2256 (1982).
Kamaike, Kazuo, et al., "Efficient methods for the synthesis of [2-$^{15}$N]guanosine and 2'-deoxy[2-$^{15}$N]guanosine derivatives," 20(1 &2) *Nucleosides, Nucleotides & Nucleic Acids* 59-75 (2001).
McGuinness, Brian F. and Koji Nakanishi, "Synthesis of Guanine Derivatives Substituted in the $O^6$-Position by Mitomycin C," 29(37) *Tetrahedron Lett.* 4673-4676.
Mehta, Jitendra R., et al., "Synthesis and properties of $O^6$-methyldeoxyguanylic acid and its copolmers with deoxycytidylic acid," 521 *Biochimica et Biophysica Acta* 770-778 (1978).
Robins, Morris J., et al., "Nucleic acid related compounds. 8. Direct conversion of 2'-Deoxyinosine to 6-Chloropurine 2'-deoxyriboside and selected 6-substituted deoxynucleosides and their evaluation as substrates of adenosine deaminase," 51(19) *Can. J. Chem.* 3161-3169 (1973).
Robins, Morris J., et al., "Nucleic acid related compounds. 33. Conversions of adenosine and guanosine to 2,6-dichloro, 2-amino-6-chloro, and derived purine nucleosides," 59(17) *Can. J. Chem.* 2601-2607 (1981).
Robins, Morris J., et al., "Nucleic acid related compounds. 34. Nonaqueous diazotization with *tert*-butyl nitrite. Introduction of fluorine, chlorine, and bromine at C-2 of purine nucleosides," 59 *Can. J. Chem.* 2608-2611 (1981).

* cited by examiner

*Primary Examiner*—Shaojia Anna Jiang
*Assistant Examiner*—Jonathan S Lau
(74) *Attorney, Agent, or Firm*—Christopher L. Wight; Ryan L. Marshall; Brinks Hofer Gilson & Lione (57) ABSTRACT

The present invention is a method for preparing 2-halo-6-aminopurines, and more specifically for preparing the clinical agent cladribine (2-chloro-2'-deoxyadenosine, CldAdo, 4), a drug of choice against hairy-cell leukemia and other neoplasms, from 2-amino-6-oxopurines, which are readily obtained from the naturally occurring compound 2'-deoxyguanosine. According to the methods of the present invention, the 6-oxo group of a protected 2'-deoxyguanosine (1) is converted to a 6-(substituted oxy) leaving group, or alternatively to a 6-chloro leaving group, the 2-amino group is replaced with a 2-chloro group, the 6-(substituted oxy) leaving group, or alternatively the 6-chloro leaving group, is replaced with a 6-amino group or, alternatively, a 2,6-dichloro substituted compound is selectively replaced with a 6-amino group, and the protecting groups are removed.

12 Claims, 2 Drawing Sheets

Figure 1

$^a$ (a) TiPBS-Cl/Et$_3$N/DMAP/CH$_2$Cl$_2$. (b) AcCl/BTEA-NO$_2$/CH$_2$Cl$_2$/−5 to 0 °C. (c) NH$_3$/MeOH/CH$_2$Cl$_2$/Δ. (d) POCl$_3$/BTEA-Cl/$N,N$-dimethylaniline/MeCN/Δ.

Figure 2

(a) TMS-Cl/BTEA-NO$_2$/CH$_2$Cl$_2$ (83%); (b) TMS-Cl/BTEA-NO$_2$/NaNO$_2$/CH$_2$Cl$_2$ (86%); (c) AcCl/BTEA-NO$_2$/CH$_2$Cl$_2$/0-5 C° (84%); (d) TMS-Br/TBN/CH$_2$Br$_2$ (85%)

METHOD FOR THE PREPARATION OF 2-HALO-2'-DEOXYADENOSINE COMPOUNDS FROM 2'-DEOXYGUANOSINE

CROSS-REFERENCE TO RELATED APPLICATIONS

This application is a 371 national phase of PCT/US2003/030386, filed Sep. 25, 2003, and claims the benefit of U.S. Provisional Application No. 60/413,915, filed Sep. 25, 2002, and U.S. Provisional Application No. 60/416,329, filed Oct. 4, 2002.

FIELD OF THE INVENTION

The present invention is directed to processes for preparing 2-halo-6-aminopurines, and more particularly to a process for preparing 2-chloro-2'-deoxyadenosine.

BACKGROUND OF THE INVENTION

The lymphoselective toxicity of 2-chloro-2'-deoxyadenosine (CldAdo, cladribine) and its potential as a chemotherapeutic agent against lymphoid neoplasms were reported by Carson et al.[1] This potent, deaminase-resistant analogue of 2'-deoxyadenosine (dAdo) is currently the drug of choice for hairy-cell leukemia.[2,3] It also has significant activity against chronic lymphocytic leukemia,[4,5] indolent non-Hodgkin's lymphoma,[6] and Waldenström's macroglobulinemia.[7] Investigations with cladribine treatment of multiple sclerosis,[8] systemic lupus erythematosis-associated glomerulonephritis,[9] and other rheumatoid and immune disorders are in progress. Cladribine is a nucleoside prodrug, which is phosphorylated by deoxycytidine kinase to CldAMP, and then sequentially to CldADP and the active CldATP.[1a,10a] Cladribine also is a good substrate for mitochondrial 2'-deoxyguanosine (dGuo) kinase,[10] and induction of programmed cell death by direct effects on mitochondria has been implicated in its potent activity against indolent lymphoid malignancies (via apoptosis) as well as in proliferating cells.[11,12]

Various methodologies have been published for the production of Cladribine. Venner reported Fischer-Helferich syntheses of naturally occurring 2'-deoxynucleosides in 1960,[13] and employed 2-chloro-2'-deoxyadenosine as an intermediate for 2'-deoxy(guanosine and inosine). Ikehara and Tada also synthesized dAdo with CldAdo as an intermediate [obtained by desulfurization of 8,2'-anhydro-9-(β-D-arabinofuranosyl)-2-chloro-8-thioadenine].[14]

Syntheses of CldAdo as a target compound have exploited the greater reactivity of leaving groups at C6 relative to those at C2 of the purine ring in $S_NAr$ displacement reactions. Robins and Robins[15] employed fusion coupling of 2,6-dichloropurine with 1,3,5-tri-O-acetyl-2-deoxy-α-D-ribofuranose. The 9-(3,5-di-O-acetyl-2-deoxy-α-D-erythro-pentofuranosyl)-2,6-dichloropurine anomer was obtained by fractional crystallization. Selective ammonolysis at C6 and accompanying deprotection gave 6-amino-2-chloro-9-(2-deoxy-α-D-erythro-pentofuranosyl)purine. The pharmacologically active β-anomer (cladribine) was prepared by an analogous coupling, chromatographic separation of anomers, and ammonolysis.[16]

Stereoselective glycosylation of sodium salts of halopurines and analogues with 2-deoxy-3,5-di-O-p-toluoyl-α-D-erythro-pentofuranosyl chloride gave β-nucleoside anomers via predominant Walden inversion,[17,18] and ammonolysis/deprotection gave CldAdo.[19] Although the sodium salt glycosylation usually gave good anomeric stereoselectivity, minor quantities of α anomers and >10% of N7 regioisomers were usually formed.[20,21] This requires separations and results in diminished yields of the desired N9 product. Carson et al.[1] had reported an enzymatic transfer of the 2-deoxy sugar from thymidine to 2-chloroadenine (ClAde). Holy and coworkers noted that cells of a strain of Escherichia coli performed glycosyl transfer from 2'-deoxyuridine to 2-chloro-6-[(dimethylaminomethylene)amino]purine to give a derivative of CldAdo.[22] Very recently Barai, Mikhailopulo, and coworkers[23] described an E. coli-mediated glycosyl transfer synthesis of 2,6-diamino-9-(3-deoxy-β-D-erythro-pentofuranosyl)purine,[24] and its enzymatic deamination to 3'-deoxyguanosine.[24] They reported glycosyl transfer from 2'-deoxyguanosine to ClAde, and claimed a yield of 81% of CldAdo (based on ClAde).[23] However, a 3:1 ratio of dGuo/ClAde was employed, so the yield of CldAdo was <27% based on dGuo.

Sampath et al. have recently shown (U.S. Pat. No. 6,596,858 B2) a method for making 2-chloro-2'-deoxyadenosine compounds, using 2-amino-2'-deoxyadenosine as a starting compound, but beginning with an initial diazotization/chloro-dediazoniation reaction on the unprotected nucleoside to replace the 2-amino group with a 2-chloro group. This method, however, creates various impurities, which requires extensive purification procedures, and results in an overall yield of only 27%.

Accordingly, there is a significant need to produce CldAdo using methods that result in a higher yield, are more cost effective, and result in a more purified form.

BRIEF SUMMARY OF THE INVENTION

The present invention is a method for producing 2-chloro-2'-deoxyadenosine (CldAdo) comprising the steps of: (a) converting the 6-oxo group of a compound having the formula (1) wherein R is a protecting group, into a 6-leaving group having sufficient reactivity for an $S_NAr$ displacement reaction; (b) replacing the 2-amino group with a 2-chloro group in a diazotization/chloro-dediazoniation reaction; (c) replacing the 6-leaving group with a 6-amino group; and (d) removing the R protecting groups, to produce 2-chloro-2'-deoxyadenosine.

DETAILED DESCRIPTION OF THE INVENTION

In accordance with the present invention, synthesis of regio- and stereochemically pure 2-chloro-2'-deoxyadenosine (Cladrabine, or CldAdo), which avoids separation of mixtures with fusion and sodium salt glycosylation procedures, is accomplished by transformation of the naturally occurring nucleoside 2'-deoxyguanosine (dGuo) as the starting compound.[24] Methods for producing CldAdo from 2'-deoxyguanosine (dGuo) according to the present invention begin with protected forms of dGuo including, but not restricted to, acyl, silyl, amide, and other derivatives useful in the field of nucleoside/nucleotide/nucleic acid chemistry and protection strategies. Methods for obtaining protected forms of dGuo are well-known in the art.[25,26,27,28,29,30] The preferred starting products for efficient synthesis of CldAdo are defined by the following chemical structure:

where R is any suitable protecting group, and preferably R is Ac or Bz.

Figure 1:
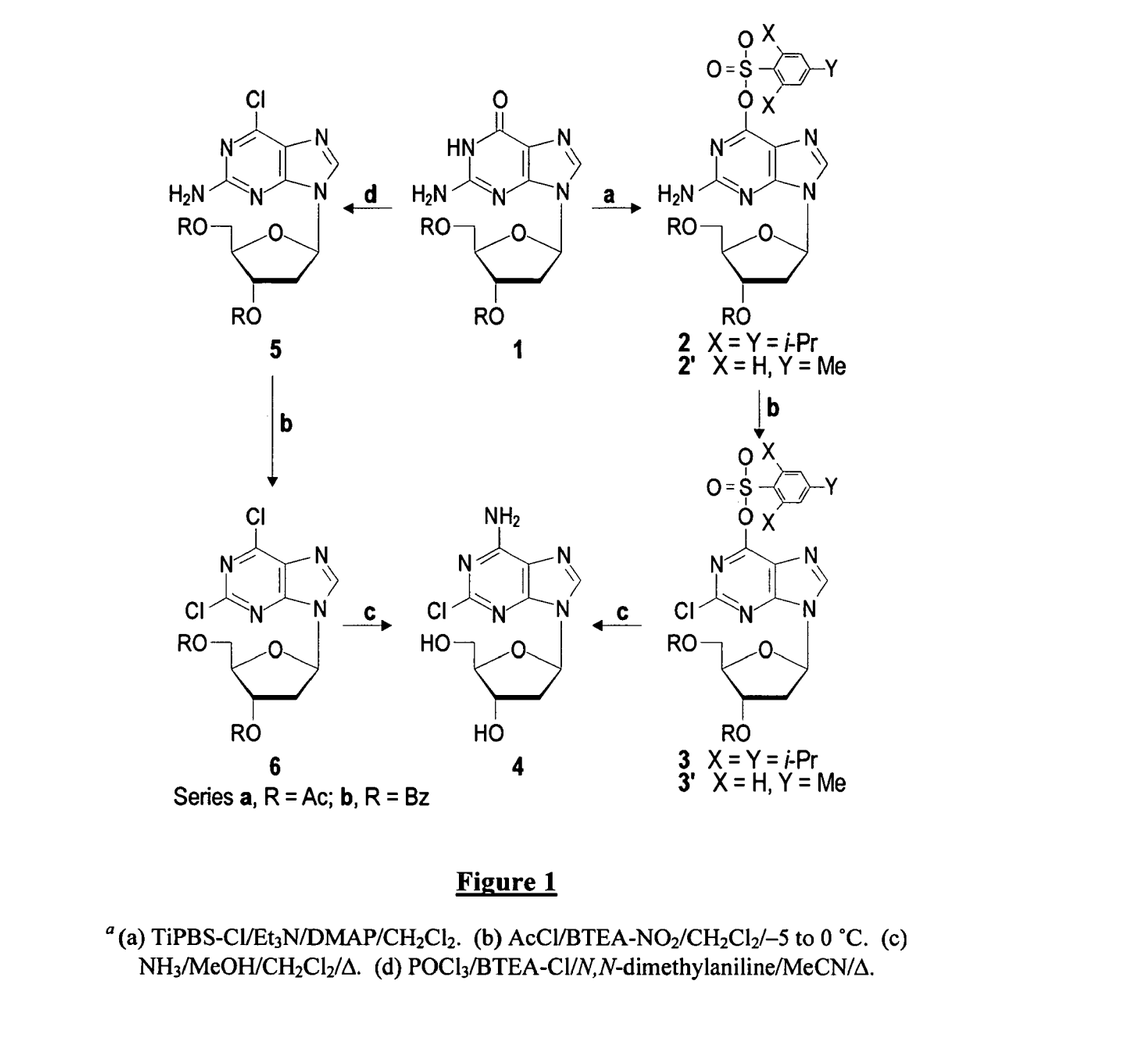
FIG. 1 shows the chemical synthesis of 2-chloro-2'-deoxyadenosine from protected forms of naturally occurring 2'-deoxyguanosine.

In order to obtain the desired CldAdo compounds, protected dGuo derivatives are treated with combinations of chemicals that effect functionalization at the C6 position to give groups that can be replaced, followed by transformation of the 2-amino function to a 2-chloro group, followed by replacement of the 6-functional group to give a 6-amino group (or a 6-substituent that can be converted into a 6-amino group, followed by conversion to the 6-amino group), and concomitant or subsequent deprotection of the resulting 6-amino-2-chloropurine derivative to give CldAdo. For example, from dGuo, CldAdo (4) (FIG. 1) is synthesized by converting the 6-oxo function into appropriate 6-(substituted oxy) leaving groups that can be replaced without protection of the 2-amino moiety, transformation of the 2-amino function to a 2-chloro functional group by diazotization/chloro-dediazoniation of the 2-amino function, and selective C6 ammonolysis of the 2-chloro-6-(substituted)purine derivatives, with accompanying sugar deprotection. This route advantageously provides retention of both β-anomeric stereochemistry and N9 isomeric purity.

Functionalization of the 6-oxo group is accomplished by converting, without protection of the 2-amino moiety, the 6-oxo group to a 6-(substituted oxy) leaving group having greater reactivity than the 2-chloro group in a $S_NAr$ displacement reaction. Two preferred methods for functionalization at the C6-oxy group include alkyl- or arylsulfonylation of the C6-oxy group and chlorodeoxygenation at C6.

Alkyl- or arylsulfonylation of the C6-oxy group can be accomplished by treating protected dGuo derivatives with (alkyl or any substituted alkyl or cycloalkyl)sulfonyl, phosphoryl or phosphonyl reagents or (aryl or any substituted aryl)sulfonyl, phosphoryl or phosphonyl reagents, which include, for example, sulfonyl compounds having the formula R'SO$_2$—X, where X is a halogen (such as chloride), imidazolide, triazolide or tetrazolide and R' is alkyl, substituted alkyl (including but not limited to fluoroalkyl), cycloalkyl, aryl, or substituted aryl, to convert the 6-oxo group to a 6-O-(alkyl, substituted alkyl, cycloalkyl, aryl or substituted aryl)sulfonyl group. In preferred embodiments, 3',5'-di-O-(acetyl or benzoyl)-2'-deoxyguanosine (1) is treated with (2,4,6-triisopropyl or 4-methyl)benzenesulfonyl chloride, to give high yields of the 6-O-arylsulfonyl derivatives 2 or 2'b. In other preferred embodiments, 1 is treated with TiPBS-Cl, which gives the 6-O-TiPBS derivative 2a or 2b, or TsCl, which gives the 6-O-Ts derivative 2'b.

Several acyl-protected 6-O-sulfonyl derivatives of dGuo that can be utilized are known in the art.[28,29,30] Treatment of 3',5'-di-O-acetyl-2'-deoxyguanosine[31] (1a) or its 3',5'-di-O-benzoyl analogue 1b[31] with TiPBS-Cl/Et$_3$N/DMAP/CHCl$_3$ by the general method of Hata et al.[29] gave the 6-O-TiPBS derivatives 2a[32] (91%) or 2b (86%), respectively. Similar treatment of 1b with TsCl/Et$_3$N/DMAP/CHCl$_3$ gave the 6-O-Ts derivative 2'b (89%). Efficient displacement of sulfonate from C6 in following steps requires a sterically hindered arylsulfonyl derivative. A more economical 6-O-tosyl derivative gave lower yields at the final stage owing to attack of ammonia at both sulfonyl sulfur and C6 (3'b gave 4 in 43% yield). By contrast, ammonolysis of the 6-O-TiPBS derivatives proceeded efficiently at C6 with minimal attack at the hindered sulfur atom. Both types of such arylsulfonate derivatives, and especially the 6-O-Ts, underwent increased nucleophilic attack at sulfur with lower temperatures (−20 to 0° C.) to give 6-oxopurine derivatives, resulting in a lower yield. However, treatment of the 6-O-TiPBS compounds with NH$_3$/MeOH/CH$_2$Cl$_2$ in a pressure tube at 80° C. strongly favored nucleophilic attack at C6 to give good yields of CldAdo (4).

Alternatively, the 6-oxo group can be replaced by a 6-chloro leaving group by chlorodeoxygenation at C6. Chlorine is the most frequently used leaving group at C6 of purine nucleosides. Methods for producing CldAdo from dGuo begin with protected forms of dGuo described above and involve treatment of such derivatives with combinations of chemicals that convert the 6-oxo function into a 6-chloro group that can be replaced on the resulting 2-amino-6-chloropurine derivative. Deoxychlorination at C6 of 1 results in excellent yields of the 2-amino-6-chloropurine derivatives 5. In preferred embodiments, protected dGuo derivatives are treated with phosphoryl chloride, a source of soluble chloride, an organic base, and acetonitrile or other compatible solvent, to convert the 6-oxo function into a 6-chloro group.

Original studies on deoxychlorination of guanosine[33] (Guo) and dGuo[34] derivatives with POCl$_3$ gave moderate (Guo) to poor (dGuo) yields of 2-amino-6-chloropurine products, and improved procedures have been reported.[26a,35,36] The acid-labile 2'-deoxy derivatives 1 were deoxychlorinated with POCl$_3$/N,N-dimethylaniline/BTEA-Cl/MeCN/Δ,[26a,36] and 6-chloro derivatives 5a (90%) and 5b (85%) were obtained in high yields under carefully controlled conditions.

Following the step of converting the 6-oxo group to a 6-(substituted oxy) leaving group, the 2-amino group is replaced with a 2-chloro group by a diazotization/halo-dediazoniation reaction. Improved methods are disclosed for replacement of an amino group on purine nucleoside derivatives with chlorine, bromine, or iodine under non-aqueous conditions by diazotization/halo-dediazoniation methods.[27] These mild diazotization/halo-dediazoniation methods are applicable at C6 of dAdo derivatives as well as at C2 of 2-amino-6-chloropurine nucleosides. In accordance with the present invention, CldAdo is produced from dGuo by treatment of protected forms of dGuo that contain a respective 6-O-(alkyl, cycloalkyl, or aryl)sulfonyl group with reagents that effect diazotization/chloro-dediazoniation at C2 to give a 2-chloro group. CldAdo is also produced by treating protected 2-amino-6-chloropurine derivatives with reagents that effect diazotization/chloro-dediazoniation at C2 to give respective 2,6-dichloropurine derivatives.

Reagents that effect diazotization/chloro-dediazoniation at C2 to give a 2-chloro group include a halide source (such as metal chlorides, metal chloride salts, acyl chlorides, sulfonyl chlorides, and silyl chlorides, alkyl and aryl substituted ammonium chloride salts, including but not limited to tetraalkyl and aryl ammonium chloride salts) and a nitrite source (such as metal nitrites, metal nitrite salts, organic nitrites, such as tert-butyl nitrite, pentyl nitrite, and isoamyl nitrite, and complex quaternary ammonium nitrites, such as benzyltriethylammonium nitrite).

In preferred embodiments of the present invention, CldAdo is synthesized by employing acetyl chloride and benzyltriethylammonium nitrite (BTEA-NO$_2$)-mediated diazotization/chloro-dediazoniation of 6-O-(2,4,6-triisopropylbenzenesulfonyl) (TIPBS) or 6-chloro derivatives that are readily obtained from dGuo. Non-aqueous diazotization/chloro-dediazoniation (acetyl chloride/benzyltriethylammonium nitrite) of 2, 2'b, or 5 gave the 2-chloropurine derivatives 3, 3'b, or 6, respectively. This new procedure for non-aqueous diazotization/chloro-dediazoniation[27] (AcCl/BTEA-NO$_2$/CH$_2$Cl$_2$/−5 to 0° C.) worked well for replacement of the 2-amino group of 2, 2'b, and 5 with chlorine to give 3a (89%), 3b (90%), 3'b (87%), 6a (95%), and 6b (91%).

Efficient diazotization/chloro-dediazoniation of 9-(2,3,5-tri-O-acetyl-β-D-ribofuranosyl)-2-amino-6-chloropurine[26, 33] (7) (FIG. 2) was effected with TMS-Cl (9 equivalents) and benzyltriethylammonium nitrite (BETA-NO$_2$) (3 equivalents) in CH$_2$Cl$_2$ at ambient temperature. The process was rapid (<30 min), and the desired 9-(2,3,5-tri-O-acetyl-β-D-ribofuranosyl)-2,6-dichloropurine[27,37] (8) (83%, without chromatography) was obtained as a white crystalline solid. Comparable yields were obtained at 0° C. TMS-Cl (3.5 equivalents) and BTEA-NO$_2$ (1.5 equivalents) with powdered NaNO$_2$ (5 equivalents) gave 8 (86%) within 1 hr. By contrast, an alternative method for non-aqueous diazotization/chloro-dediazoniation of 7 employed Cl$_2$/TBN/CuCl in a strongly exothermic reaction, and removal of colloidal material by filtration was required prior to crystallization of 7.[35]

Figure 2:
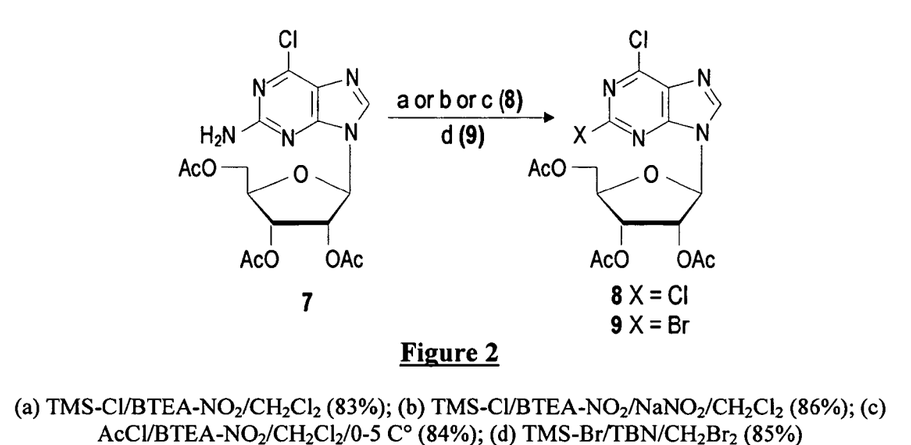
FIG. 2 shows the diazotization/halo-dediazoniation conversion reaction from a 2-aminopurine nucleoside to a 2-halopurine nucleoside.

Compound 7 underwent efficient diazotization/bromo-dediazoniation with TMS-Br and tert-butyl nitrite (TBN). Competing redox interactions between nitrite anion and TMS-Br precluded the use of NaNO$_2$. The 2-bromo-6-chloropurine nucleoside 3[27,37] (85%, without chromatography) was obtained as a crystalline solid with TMS-Br (9 equivalents)/TBN (20 equivalents)/CH$_2$Br$_2$/ambient temperature within 1 h.

NOCl/CH$_2$Cl$_2$ or NOBr/CH$_2$Br$_2$ is presumed to be generated from (Me$_3$SiX or AcCl) and (TBN or BTEA-NO$_2$). These procedures provide efficient diazotization/halo-dediazoniation of protected (2 or 6)-aminopurine nucleosides as well as the acid-sensitive 2'-deoxynucleosides. The reactions are cost-effective and proceed at or below ambient temperature with convenient reagents and standard laboratory equipment and conditions.

Following replacement of the 2-amino group with a 2-chloro group, the protected forms of dGuo that contain a respective 6-O-(alkyl, cycloalkyl, or aryl)sulfonyl or phosphoryl group and a 2-chloro group is reacted with chemicals that cause replacement of the 6-O-(alkyl, cycloalkyl, or aryl) sulfonyl or phorphoryl group to give a 6-amino group (or a substituent that can be converted into a 6-amino group, resulting in overall conversion of the substituent into a 6-amino group) of a resulting 6-amino-2-chloropurine derivative. In preferred embodiments, the 6-leaving group is replaced with a 6-amino group by reacting the product of step (b) with a nitrogen source capable of being converted to an amino group in a solvent compatible with the nitrogen source to replace the 6-leaving group with a 6-amino group by selective ammonolysis of the 6-leaving group. The nitrogen source is selected from the group consisting of ammonia, azides, hydrazines, benzylic amines, or compatible ammonium salts. The solvent may be any solvent that is compatible with the nitrogen source, such as methanol, ethanol, higher alcohols, or aprotic solvents, such as 1,2-dimethoxyethane, tetrahydrofuran, or DMF.

In other preferred embodiments, the respective 6-O-(alkyl, cycloalkyl, or aryl)sulfonyl leaving group is reacted with ammonia in a compatible aprotic solvent to give a 6-amino-2-chloropurine derivative, followed by deprotection (if necessary) to give CldAdo. In a more preferred embodiment, a 9-(3,5-di-O-acyl-β-D-erythro-pentofuranosyl-6-O-(alkyl, cycloalkyl, or aryl)sulfonyl-2-chloropurine is treated with ammonia in methanol or other compatible solvent to give CldAdo.

Further, protected derivatives of 2,6-dichloropurine are treated with reagents that cause selective replacement of the 6-chloro group to give a 6-amino group (or a substituent that can be converted into a 6-amino group, followed by conversion of the substituent into a 6-amino group) of a resulting 6-amino-2-chloropurine derivative. In a more preferred embodiment, 9-(3,5-di-O-acyl-β-D-erythro-pentofuranosyl)-2,6-dichloropurine is treated with ammonia in methanol or other compatible solvent to give CldAdo.

Selective ammonolysis at C6 (arylsulfonate with 3 or chloride with 6) and accompanying deprotection of the sugar moiety gave CldAdo (4) (64-75% overall from 1). Specifically, displacements of the hindered arylsulfonate (from 3) or chloride (from 6) at C6 with accompanying cleavage of the sugar esters were effected at 80° C. with NH$_3$/MeOH/CH$_2$Cl$_2$. Cladribine (4) was obtained in high yields from 3a (81%), 3b (83%), 6a (87%), and 6b (94%), but only in moderate yield from the 6-O-tosyl derivative 3'b (43%).

The R protecting groups are removed by deacylation using a basic reagent well known in the art in a solvent compatible with the basic reagent, to remove the R protecting groups and produce 2-chloro-2'-deoxyadenosine. The basic reagent is selected from the group consisting of ammonia, metal alkoxides, metal hydroxides, and metal carbonates. The solvent may be any solvent that is compatible with the basic reagent, such as methanol, ethanol, 1,2-dimethoxyethane/H$_2$O, or tetrahydrofuran/H$_2$O.

It is to be noted that removal of the R protecting groups may occur concomitantly with or subsequent to the replacement of the 6-(substituted oxy) leaving group with a 6-amino group by ammonolysis. Both steps of replacement of the 6-(substituted oxy) leaving group with a 6-amino group and removal of the R protecting groups is accomplished by use of a nitrogen source in a solvent compatible with the nitrogen source. Where the nitrogen source is ammonia in a protic solvent, such as methanol or ethanol, both steps proceed simultaneously. However, where the nitrogen source is anhydrous ammonia in a dry solvent, such as 1,2-dimethoxyethane, or tetrahydrofuran, only the step of replacement of the 6-(substituted oxy) leaving group with a 6-amino group proceeds. In this case, it is necessary and sometimes desirable to remove the R protecting groups in a separate step.

In the most preferred embodiments of the present invention, synthesis of the clinical drug cladribine (2-chloro-2'-deoxyadenosine, CldAdo, 4) was accomplished in three steps from the readily available 3',5'-di-O-acetyl-2'-deoxyguanosine (1a) or its dibenzoyl analogue 1b. Replacement of the 2-amino group proceeded in high yields by diazotization/chloro-dediazoniation with AcCl/BTEA-NO$_2$. Selective ammonolysis of 3a and 3b (6-OTiPBS) or 6 (6-Cl), with accompanying deacylation, gave 4 (64-75% overall). Ammonolysis of 3'b (6-OTs) was problematic and gave 4 in poor overall yield (33%). Routes that employed deoxychlorination of 1 were ~10% more efficient overall than those which involved 6-O-TiPBS intermediates.

EXAMPLES

Melting points for 4 were determined with a hot-stage apparatus. UV spectra were recorded with solutions in MeOH. $^1$H NMR spectra were recorded at 300 MHz with solutions in CDCl$_3$ unless otherwise indicated. "Apparent" peak shapes are in quotation marks when first-order splitting should be more complex or when peaks were poorly resolved. Mass spectra (MS) were determined with FAB (glycerol) unless otherwise indicated. Chemicals and solvents were of reagent quality. CH$_2$Cl$_2$ and MeCN were dried by reflux over and distillation from CaH$_2$. CHCl$_3$ was dried over P$_2$O$_5$ and distilled. AcCl, POCl$_3$, and N,N-dimethylaniline were freshly distilled before use. Benzyltriethylammonium nitrite (BTEA-NO$_2$) was prepared from BTEA-Cl by ion exchange [Dowex 1×2 (NO$_2^-$)]. Column chromatography (silica gel, 230-400 mesh) was performed with CH$_2$Cl$_2$/MeOH. Compounds 1a and 1b were prepared as described.[31]

Method 1 (nucleoside/TiPBS-Cl/DMAP/Et$_3$N/CHCl$_3$) is described for 1a→2a, method 2 (nucleoside/AcCl/BTEA-NO$_2$/CH$_2$Cl$_2$) for 2a→3a, method 3 (nucleoside/N,N-dimethylaniline/POCl$_3$/BTEA-Cl/MeCN) for 1a→5a, and method 4 (nucleoside/NH$_3$/MeOH/Δ) for 3a→4. Analogous reactions with equivalent molar proportions of other nucleosides gave the indicated products and quantities.

Example 1

Preparation of 9-(3,5-Di-O-acetyl-2-deoxy-β-D-erythro-pentofuranosyl)-2-amino-6-O-(2,4,6-triisopropylbenzenesulfonyl)purine (2a)

Method 1. Et$_3$N (1.25 mL, 910 mg, 9.0 mmol) was added to a stirred solution of 1a (1.67 g, 4.8 mmol), TiPBS-Cl (2.73 g, 9.0 mmol), and DMAP (72 mg, 0.6 mmol) in dried CHCl$_3$ (70 mL) under N$_2$. Stirring was continued for 24 h, and volatiles were evaporated. The orange residue was chromatographed (CH$_2$Cl$_2$/MeOH) give 2a[32] (2.67 g, 91%) as a slightly yellow foam with UV max 238, 291 nm, min 264 nm; $^1$H NMR (500 MHz) δ 1.26-1.32 (m, 18H), 2.08 (s, 3H), 2.14 (s, 3H), 2.54 (ddd, J=4.7, 9.0, 14.0 Hz, 1H), 2.91-2.99 (m, 2H), 4.22-4.37 (m, 3H), 4.43-4.47 (m, 2H), 4.97 (br s, 2H), 5.41-5.42 ("d", 1H), 6.26-6.29 (m, 1H), 7.21 (s, 2H), 7.84 (s, 1H); LRMS m/z 618 (MH$^+$[C$_{29}$H$_{40}$N$_5$O$_8$S]=618); HRMS m/z 640.2413 (MNa$^+$[C$_{29}$H$_{39}$N$_5$O$_8$SNa]=640.2417).

Example 2

Preparation of 2-Amino-9-(3,5-di-O-benzoyl-2-deoxy-β-D-erythro-pentofuranosyl)-6-O-(2,4,6-triisopropylbenzenesulfonyl) purine (2b)

Treatment of 1b (950 mg, 2.0 mmol) by method 1 gave 2b (1.27 g, 86%) as a white solid foam with UV max 289 nm, min 264 nm; $^1$H NMR δ 1.29-1.32 (m, 18H), 2.76 (ddd, J=2.1, 6.0, 14.3 Hz, 1H), 2.96 ("quint", J=6.8 Hz, 1H), 3.15-3.25 (m, 1H), 4.34 ("quint", J=6.8 Hz, 2H), 4.65-4.74 (m, 2H), 4.85-4.90 (m, 1H), 5.00 (br s, 2H), 5.84-5.86 ("d", 1H), 6.38-6.43 (m, 1H), 7.30 (s, 2H), 7.44-7.55 (m, 4H), 7.58-7.69 (m, 2H), 7.85 (s, 1H), 8.04 (d, J=7.1 Hz, 2H), 8.11 (d, J=7.1 Hz, 2H); LRMS m/z 742 (MH$^+$[C$_{39}$H$_{44}$N$_5$O$_8$S]=742), 764 (MNa$^+$[C$_{39}$H$_{43}$N$_5$O$_8$SNa]=764); HRMS m/z 764.2730 (MNa$^+$[C$_{39}$H$_{43}$N$_5$O$_8$SNa]=764.2730).

Example 3

Preparation of 2-Amino-9-(3,5-di-O-benzoyl-2-deoxy-β-D-erythro-pentofuranosyl)-6-O-(4-methylbenzenesulfonyl)purine (2'b)

Et$_3$N (700 μL, 506 mg, 5.0 mmol) was added to a stirred solution of 1b (1.43 g, 3.0 mmol), TsCl (858 mg, 4.5 mmol), and DMAP (36 mg, 0.3 mmol) in dried CHCl$_3$ (45 mL) under N$_2$. Stirring was continued for 15 h, and volatiles were evaporated. The slightly yellow residue was chromatographed (CH$_2$Cl$_2$/MeOH) to give 2'b (1.68 g, 89%) as a white solid foam with UV max 300 nm; $^1$H NMR (DMSO-d$_6$) δ 2.43 (s, 3H), 2.73 (ddd, J=2.1, 8.4, 14.4 Hz, 1H), 3.17-3.27 ("quint", J=7.2 Hz, 1H), 4.52-4.65 (m, 3H), 5.76-5.78 ("d", 1H), 6.37-6.41 (m, 1H), 6.95 (br s, 2H), 7.47-7.73 (m, 8H), 7.95 (d, J=7.8 Hz, 2H), 8.03-8.11 (m, 4H), 8.30 (s, 1H); LRMS m/z 630 (MH$^+$[C$_{31}$H$_{28}$N$_5$O$_8$S]=630), m/z 652 (MNa$^+$[C$_{31}$H$_{27}$N$_5$O$_8$SNa]=652); LRMS m/z 652.1467 (MNa$^+$[C$_{31}$H$_{27}$N$_5$O$_8$SNa]=652.1478).

Example 4

Preparation of 9-(3,5-Di-O-acetyl-2-deoxy-β-D-erythro-pentofuranosyl)-2-chloro-6-O-(2,4,6-triisopropylbenzenesulfonyl)purine (3a)

Method 2. A solution of AcCl (200 μL, 220 mg, 2.8 mmol) in dried CH$_2$Cl$_2$ (12 mL) under N$_2$ was chilled in a NaCl/ice/H$_2$O bath (−5 to 0° C.) for 15 min. BTEA-NO$_2$ (520 mg, 2.2 mmol) was dissolved in dried CH$_2$Cl$_2$ (8 mL) and this solution was immediately added dropwise to the cold, stirred solution of AcCl/CH$_2$Cl$_2$. A solution of 2a (288 mg, 0.5 mmol) in dried CH$_2$Cl$_2$ (5 mL) was then added dropwise to the cold solution, and stirring was continued for 5 min (TLC, CH$_2$Cl$_2$/MeOH, 95:5, showed complete conversion of 2a into a single product). The reaction mixture was added dropwise at a rapid rate to a cold (ice/H$_2$O bath), vigorously stirred mixture of saturated NaHCO$_3$/H$_2$O (100 mL)//CH$_2$Cl$_2$ (100 mL). The layers were separated, and the organic phase was washed with cold (0° C.) H$_2$O (2×100 mL) and dried (MgSO$_4$) for 1 h. Volatiles were evaporated, and the residue was chromatographed (CH$_2$Cl$_2$/MeOH) to give 3a (267 mg, 89%) as a white solid foam with UV max 240, 266 nm, min 255 nm; $^1$H NMR (500 MHz) δ 1.24-1.31 (m, 18H), 2.08 (s, 3H), 2.13 (s, 3H), 2.67 (ddd, J=2.5, 7.0, 15.5 Hz, 1H), 2.76-2.81 (m, 1H), 2.90-2.96 ("quint", J=7.0 Hz, 1H), 4.28-4.33 ("quint", J=7.0 Hz, 2H), 4.35-4.39 (m, 3H), 5.38-5.39 ("d", 1H), 6.42-6.45 (m, 1H), 7.22 (s, 2H), 8.23 (s, 1H); LRMS m/z 637 (MH$^+$[C$_{29}$H$_{38}$ClN$_4$O$_8$S]=637); HRMS m/z 659.1902 (MNa$^+$[C$_{29}$H$_{37}$ClN$_4$O$_8$SNa]=659.1918).

Example 5

Preparation of 9-(3,5-Di-O-benzoyl-2-deoxy-β-D-erythro-pentofuranosyl)-2-chloro-6-O-(2,4,6-triisopropylbenzenesulfonyl)purine (3b)

Treatment 2b (1.20 g, 1.6 mmol) by method 2 gave 3b (1.10 g, 90%) as a yellow solid foam with UV max 230, 266 nm, min 255 nm; $^1$H NMR δ 1.22-1.34 (m, 18H), 2.92-3.00 (m, 3H), 4.30-4.34 (m, 3H), 4.68-4.77 (m, 3H), 5.80-5.82 ("d", 1H), 6.54-6.57 (m, 1H), 7.42-7.64 (m, 8H), 8.00 (d, J=8.4 Hz, 2H), 8.10 (d, J=8.4 Hz, 2H), 8.26 (s, 1H); HRMS m/z 783.2224 (MNa$^+$[C$_{39}$H$_{41}$ClN$_4$O$_8$SNa]=783.2231).

Example 6

Preparation of 9-(3,5-Di-O-benzoyl-2-deoxy-β-D-erythro-pentofuranosyl)-2-chloro-6-O-(4-methylbenzenesulfonyl)purine (3'b)

Treatment of 2'b (1.45 g, 2.3 mmol) by method 2 gave 3'b (1.30 g, 87%) as a slightly yellow foam with UV max 267 nm, min 255 nm; $^1$H NMR (DMSO-$d_6$) δ 2.45 (s, 3H), 2.86 (ddd, J=3.4, 6.2, 14.0 Hz, 1H), 3.21-3.30 ("quint", J=7.0 Hz, 1H), 4.55-4.67 (m, 3H), 5.82-5.84 (m, 1H), 6.56-6.61 (m, 1H), 7.42-7.72 (m, 8H), 7.88 (d, J=7.8 Hz, 2H), 8.04-8.07 (m, 4H), 8.88 (s, 1H); HRMS m/z 671.0983 (MNa$^+$ [$C_{31}H_{25}ClN_4O_8SNa$]=671.0979).

Example 7

Preparation of 9-(3,5-Di-O-acetyl-2-deoxy-β-D-erythro-pentofuranosyl)-2-amino-6-chloropurine (5a) Method 3

A mixture of 1a (540 mg, 1.54 mmol), BTEA-Cl (710 mg, 3.1 mmol), N,N-dimethylaniline (215 μL, 206 mg, 1.7 mmol), and POCl$_3$ (720 μL, 1.2 g, 7.7 mmol) in MeCN (6 mL) was stirred in a preheated oil bath (85° C.) for 10 min. Volatiles were flash evaporated immediately (in vacuo), and the yellow foam was dissolved (CHCl$_3$, 15 mL) and stirred vigorously with crushed ice for 15 min. The layers were separated, and the aqueous phase was extracted (CHCl$_3$, 3×5 mL). Crushed ice was frequently added to the combined organic phase, which was washed [(ice-H$_2$O (3×5 mL), 5% NaHCO$_3$/H$_2$O (to pH ~7)] and dried (MgSO$_4$). Volatiles were evaporated, and the residue was chromatographed (CH$_2$Cl$_2$/MeOH) to give 5a[36,38] (517 mg, 90%) as a white solid foam with UV max 248, 310 nm, min 268 nm; $^1$H NMR (500 MHz, DMSO-$d_6$) δ 2.02 (s, 3H), 2.08 (s, 3H), 2.49-2.52 (m, 1H), 3.04-3.06 (m, 1H), 4.20-4.29 (m, 3H), 5.32-5.34 ("d", 1H), 6.23-6.26 (m, 1H); 7.03 (br s, 2H), 8.35 (s, 1H); $^1$H NMR δ 2.03 (s, 3H), 2.08 (s, 3H), 2.51 (ddd, J=2.7, 5.9, 14.2 Hz, 1H), 2.85-2.94 ("quint", J=7.1 Hz, 1H), 4.28-4.42 (m, 3H), 5.35-5.37 (m, 1H), 6.21-6.26 (m, 1H), 7.89 (s, 1H); HRMS (EI) m/z 369.0844 (M$^+$[$C_{14}H_{16}ClN_5O_5$]=369.0840).

Example 8

Preparation of 2-Amino-9-(3,5-di-O-benzoyl-2-deoxy-β-D-erythro-pentofuranosyl)-6-chloropurine (5b)

Treatment of 1b (2.38 g, 5 mmol) by method 3 gave 5b (2.10 g, 85%) as a slightly yellow solid foam with UV max 310 nm; $^1$H NMR (DMSO-$d_6$) δ 2.69-2.78 ("ddd", 1H), 3.20-3.24 ("quint", J=7.2 Hz, 1H), 4.56-4.67 (m, 3H), 5.77-5.79 ("d", 1H), 6.39-6.44 (m, 1H), 7.02 (br s, 2H), 7.48-7.71 (m, 6H), 7.96 (d, J=8.4 Hz, 2H), 8.06 (d, J=8.7 Hz, 2H), 8.37 (s, 1H); LRMS m/z 494 (MH$^+$[$C_{24}H_{21}ClN_5O_5$]=494); HRMS m/z 516.1042 (MNa$^+$[$C_{24}H_{20}ClN_5O_5Na$]=516.1051).

Example 9

Preparation of 9-(3,5-Di-O-acetyl-2-deoxy-β-D-erythro-pentofuranosyl)-2,6-dichloropurine (6a)

Treatment of 5a (265 mg, 0.7 mmol) by method 2 gave 6a[39] (266 mg, 95%) as a white solid foam with UV max 274 nm, min 232 nm; $^1$H NMR (500 MHz) δ 2.12 (s, 3H), 2.15 (s, 3H), 2.73 (dddd, J=2.4, 5.9, 14.2 Hz, 1H), 2.83-2.86 (m, 1H), 4.38-4.39 (m, 3H), 5.41-5.42 ("d", 1H), 6.45-6.50 (m, 1H), 8.33 (s, 1H); HRMS m/z 411.0230 (MNa$^+$ [$C_{14}H_{14}Cl_2N_4O_5Na$]=411.0239).

Example 10

Preparation of 9-(3,5-Di-O-benzoyl-2-deoxy-β-D-erythro-pentofuranosyl)-2,6-dichloropurine (6b)

Treatment of 5b (407 mg, 0.8 mmol) by method 2 gave 6b (386 mg, 91%) as a slightly yellow solid foam with UV max 274 nm, min 257 nm; $^1$H NMR (500 MHz, DMSO-$d_6$) δ 2.87 (ddd, J=3.5, 8.0, 17.5 Hz, 1H), 3.25-3.31 (m, 1H), 4.57-4.71 (m, 3H), 5.83-5.85 ("d", 1H), 6.59-6.62 (m, 1H), 7.46-7.72 (m, 6H), 7.91 (d, J=7.5 Hz, 2H), 8.09 (d, J=7.5 Hz, 2H), 8.96 (s, 1H); HRMS m/z 535.0562 (MNa$^+$[$C_{24}H_{18}Cl_2N_4O_5Na$]= 535.0552).

Example 11

Preparation of 2-Chloro-2'-deoxyadenosine (Cladribine, 4) Method 4

NH$_3$/MeOH (12 mL, saturated at 0° C.) was added to a solution of 3a (159 mg, 0.25 mmol) in CH$_2$Cl$_2$ (8 mL) in a pressure tube. The tube was sealed and immediately immersed in an oil bath preheated to 80° C. Heating (80° C.) was continued for 7 h, and volatiles were evaporated. The residue was dissolved (H$_2$O, 2 mL), and the solution was applied to a column of Dowex 1×2 (OH$^-$, 20 mL), the flask was rinsed (H$_2$O, 5 mL) and applied to the column. The column was washed (H$_2$O) until the pH of the eluate was neutral, and then MeOH/H$_2$O (1:1) was applied. UV-absorbing fractions were pooled, and volatiles were evaporated. EtOH (3×10 mL) was added and evaporated, and the residue was dried (in vacuo) to give 4 (58 mg, 81%). The white powder was recrystallized from MeOH to give 4 (2 crops, 84% recovery) with mp >300° C. (crystals slowly became brown at ~220° C.), or from H$_2$O (2 crops, 72% recovery) with mp >300° C. (Lit. mp softening at 210-215 ° C.,[16] then dec.; >300° C.;[18,21] 232° C.); UV, $^1$H NMR, and MS data were in agreement with published values.[21,22] Anal. Calcd for $C_{10}H_{12}ClN_5O_3$: C, 42.04; H, 4.23; N, 24.51. Found: C, 41.85; H, 4.40; N, 24.46.

Treatment of 3b (83%), 3'b (43%), 6a (87%), or 6b (94%) by method 4 gave 4 as white, TLC homogeneous powders with identical spectral data.

Example 12

Preparation of 9-(2,3,5-Tri-O-acetyl-β-D-ribofuranosyl)-2,6-dichloropurine (8)

Method A. TMS-Cl (1.14 mL, 978 mg, 9.0 mmol) was added dropwise to a stirred solution of 7 (428 mg, 1.0 mmol) in CH$_2$Cl$_2$ (30 mL) under N$_2$. BTEA-NO$_2$ (714 mg, 3.0 mmol) in CH$_2$Cl$_2$ (10 mL) was added dropwise (1 drop/2 sec) and the solution was stirred at ambient temperature for 30 min (TLC). The solution was diluted (CH$_2$Cl$_2$, 200 mL) and washed (5% NaHCO$_3$/H$_2$O, 5×100 mL). The combined aqueous phase was extracted (CH$_2$Cl$_2$, 2×100 mL), and the combined organic phase was dried (MgSO$_4$) and filtered. Volatiles were evaporated, Et$_2$O was added to and evaporated (3×25 mL) from the yellow oil, and the residue was recrystallized (EtOH) to give 8 (373 mg, 83%) as pale-yellow crystals with mp, UV, $^1$H NMR, and MS data as reported.[27]

Method B. TMS-Cl (444, uL, 280 mg, 3.50 mmol) was added to dropwise to a stirred mixture of 7 (428 mg, 1.0 mmol) and powdered $NaNO_2$ (345 mg, 5.0 mmol) in $CH_2Cl_2$ (25 mL) under $N_2$. BTEA-$NO_2$ (357 mg, 1.5 mmol) in $CH_2Cl_2$ (25 mL) was added dropwise (1 drop/sec) and the solution was stirred at ambient temperature for 1 h (TLC). The mixture was cooled for 15 min and added dropwise to a cold, vigorously stirred mixture of saturated $NaHCO_3/H_2O$ (200 mL)/$CH_2Cl_2$ (200 mL). The aqueous layer was extracted ($CH_2Cl_2$ 100 mL), and the combined organic phase was washed ($H_2O$, 100 mL) and dried $MgSO_4$). Volatiles were evaporated, and the yellow oil was recrystallized (BuOH) to give 8 (384 mg, 85%) as pale-yellow crystals.

Method C. A solution of AcCl/$CH_2Cl_2$ (1M, 2.5mL, 2.5 mmol) was added to dried $CH_2Cl_2$ (10 mL) under $N_2$, and the solution was cooled for 15 min. BTEA-$NO_2$ (535.5 mg, 2.25 mmol) in $CH_2Cl_2$ (5 mL) was then added dropwise (1 drop/2 sec) to the cold, stirred solution of AcCl/$CH_2Cl_2$. A cold solution of 7 (214 mg., 0.5 mmol) in dried $CH_2Cl_2$ (5 mL) was then added dropwise to the cooled, stirred AcCl/BETA-$NO_2Cl_2$ solution (TLC, hexanes/EtOAc, 3:7). Immediate workup and recrystallization (as in method B) gave 8 (187 mg, 84%) as pale-yellow crystals.

ENDNOTES

[1] (a) Carson, D. A.; Wasson, D. B.; Kaye, J.; Ullman, B.; Martin, D. W., Jr.; Robins, R. K.; Montgomery, J. A. Proc. Natl. Acad. Sci. USA 1980, 77, 6865-6869. (b) Carson, D. A.; Wasson, D. B.; Taetle, R.; Yu, A. Blood 1983, 62, 737-743.

[2] Piro, L. D., Carrera, C. J.; Carson, D. A.; Beutler, E. N. Engl. J. Med. 1990, 322, 1117-1121.

[3] Jehn, U.; Bartl, R.; Dietzfelbinger, H.; Vehling-Kaiser, U.; Wolf-Hornung, B.; Hill, W.; Heinemann, V. Ann. Hematol. 1999, 78, 139-144.

[4] Piro, L. D.; Carrera, C. J.; Beutler, E., Carson, D. A. Blood 1988, 72, 1069-1073.

[5] Mitterbauer, M.; Hilgenfeld, E.; Wilfing, A.; Jäger, U.; Knauf, W. U. Leukemia 1997, 11, Suppl. 2, S35-S37.

[6] Kong, L. R.; Huang, C.-F.; Hakimian, D.; Variakojis, D.; Klein, L.; Kuzel, T. M.; Gordon, L. I.; Zanzig, C.; Wollins, E.; Tallman, M. S. Cancer 1998, 82, 957-964.

[7] Hellmann, A.; Lewandowski, K.; Zaucha, J. M.; Bieniaszewska, M.; Halaburda, K.; Robak, T. Eur. J. Haematol. 1999, 63, 35-41.

[8] Beutler, E.; Sipe, J.; Romine, J.; McMillan, R.; Zyroff, J.; Koziol, J. Semin. Hematol. 1996, 33, Suppl. 1, 45-52.

[9] Davis, J. C., Jr.; Austin, H., III; Boumpas, D.; Fleisher, T. A.; Yarboro, C.; Larson, A.; Balow, J.; Klippel, J. H.; Scott, D. Arthritis Rheum. 1998, 41, 335-343.

[10] (a) Wang, L.; Karlsson, A.; Arnér, E. S. J.; Eriksson, S. J. Biol. Chem. 1993, 268, 22847-22852. (b) Sjöberg, A. H.; Wang, L.; Eriksson, S. Mol. Pharmacol. 1998, 53, 270-273.

[11] Genini, D.; Adachi, S.; Chao, Q.; Rose, D. W.; Carrera, C. J.; Cottam, H. B.; Carson, D. A.; Leoni, L. M. Blood, 2000, 96, 3537-3543.

[12] Marzo, I.; Pérez-Galán, P.; Giraldo, P.; Rubio-Félix, D.; Anel, A.; Naval, J. Biochem. J. 2001, 359, 537-546.

[13] Venner, H. Chem. Ber. 1960, 93, 140-149.

[14] Ikehara, M.; Tada, H. J. Am. Chem. Soc. 1965, 87, 606-610.

[15] Robins, M. J.; Robins, R. K. J Am. Chem. Soc. 1965, 87, 4934-4940.

[16] Christensen, L. F.; Broom, A. D.; Robins, M. J.; Bloch, A. J. Med. Chem. 1972, 15, 735-739.

[17] Seela, F.; Kehne, A. Liebigs Ann. Chem. 1983, 876-884.

[18] Kazimierczuk, Z.; Cottam, H. B.; Revankar, G. R.; Robins, R. K. J. Am. Chem. Soc. 1984, 106, 6379-6382.

[19] Robins, R. K.; Revankar, G. R. U.S. Pat. No. 4,760,137, 1988; also see Chem. Abstr. 1986, 105, 60911u.

[20] Hildebrand, C.; Wright, G. E. J. Org. Chem. 1992, 57, 1808-1813.

[21] Worthington, V. L.; Fraser, W.; Schwalbe, C. H. Carbohydr. Res. 1995, 275, 275-284.

[22] Votruba, I.; Holy, A.; Dvoráková, H.; Gunter, J.; Hocková, D.; Hrebabecky, H.; Cihlár, T.; Masojídková, M. Collect. Czech. Chem. Commun. 1994, 59, 2303-2330.

[23] Barai, V. N.; Zinchenko, A. I.; Eroshevskaya, L. A.; Zhernosek, E. V.; De Clercq, E.; Mikhailopulo, I. A. Helv. Chim. Acta 2002, 85, 1893-1900.

[24] Robins, M. J.; Zou, R.; Hansske, F.; Wnuk, S. F. Can. J. Chem. 1997, 75, 762-767.

[25] Barai, V. N.; Zinchenko, A. I.; Eroshevskaya, L. A.; Kalinichenko, E. N.; Kulak, T. I.; Mikhailopulo, I. A. Helv. Chim. Acta 2002, 85, 1901-1908.

[26] (a) Robins, M. J.; Uznanski, B. Can. J. Chem. 1981, 59, 2601-2607. (b) Robins, M. J.; Uznanski, B. Can. J. Chem. 1981, 59, 2608-2611.

[27] Francom, P., Janeba, Z.; Shibuya, S.; Robins, M. J. J. Org. Chem., 2002, 67, 6788-6796.

[28] (a) Bridson, P. K.; Markiewicz, W.; Reese, C. B. J. Chem. Soc., Chem. Commun. 1977, 447-448. (b) Bridson, P. K.; Markiewicz, W. T.; Reese, C. B. J. Chem. Soc., Chem. Commun. 1977, 791-792.

[29] Daskalov, H. P.; Sekine, M.; Hata, T. Tetrahedron Lett. 1980, 21, 3899-3902.

[30] Gaffney, B. L.; Jones, R. A. Tetrahedron Lett. 1982, 23, 2253-2256.

[31] Matsuda, A.; Shinozaki, M; Suzuki, M.; Watanabe, K.; Miyasaka, T. Synthesis 1986, 385-386

[32] McGuinness, B. F.; Nakanishi, K.; Lipman, R.; Tomasz, M. Tetrahedron Lett. 1988, 29, 4673-4676.

[33] Gerster, J. F.; Jones, J. W.; Robins, R. K. J. Org. Chem. 1963, 28, 945-948.

[34] Mehta, J. R.; Ludlum, D. B. Biochim. Biophys. Acta 1978, 521, 770-778.

[35] Nandanan, E.; Camaioni, E.; Jang, S.-Y.; Kim, Y.-C.; Cristalli, G.; Herdewijn, P.; Secrist, J. A., III; Tiwari, K. N.; Mohanram, A.; Harden, T. K.; Boyer, J. L.; Jacobson, K. A. J. Med. Chem. 1999, 42, 1625-1638.

[36] Kamaike, K.; Kinoshita, K.; Niwa, K.; Hirose, K.; Suzuki, K.; Ishido, Y. Nucleosides, Nucleotides, Nucleic Acids 2001, 20, 59-75.

[37] Nair, V.; Richardson, S G. Synthesis 1982, 670-672.

[38] Montgomery, J. A.; Hewson, K. J. Med. Chem. 1969, 12, 498-504.

[39] Gerster, J. F.: Jones, J. W.; Robins, R. K., J. Org. Chem. 1963, 23, 945-948.

We claim:

1. A method for producing 2-chloro-2'-deoxyadenosine comprising the steps of:
   (a) converting the 6-oxo group of a compound having the formula wherein R is a protecting group selected from the group consisting of acyl and silyl, into a 6-(substituted oxy) group having sufficient reactivity in an $S_NAr$ displacement reaction wherein the 6-(substituted oxy) group is selected from the group consisting of alkylsulfonyl, arylsulfonyl, and chloride;

(b) replacing the 2-amino group with a 2-chloro group by a diazotization/chloro-dediazoniation reaction;

(c) replacing the 6-(substituted oxy) leaving group with a 6-amino group; and

(d) removing the R protecting groups, to produce 2-chloro-2'-deoxyadenosine;

wherein replacing the 2-amino group with a 2-chloro group by a diazotization/chloro-dediazoniation reaction is performed using acetyl chloride and benzyltriethylammonium nitrite.

2. The method according to claim 1, wherein the diazotization/chloro-dediazoniation reaction is performed at or less than a temperature of 0° C. and sufficient to carry out the reaction.

3. A method for producing 2-chloro-2'-deoxyadenosine comprising the steps of:

(a) converting the 6-oxo group of a compound having the formula wherein R is a protecting group selected from the group consisting of acyl and silyl, into a 6-(substituted oxy) leaving group selected from the group consisting of (alkyl or fluoroalkyl or cycloalkyl)-sulfonyl, -phosphoryl or -phosphonyl groups, (aryl or 4-methylbenzene or 2,4,6-triisopropylbenzene)-sulfonyl, -phosphoryl or -phosphonyl groups;

(b) replacing the 2-amino group of the product of step (a) with a 2-chloro group;

(c) replacing the 6-(substituted oxy) leaving group of the product of step (b) with a 6-amino group; and

(d) removing the R protecting groups, to produce 2-chloro-2'-deoxyadenosine;

wherein replacing the 2-amino group of the product of step (a) with a 2-chloro group is performed using acetyl chloride and benzyltriethylammonium nitrite.

4. The method according to claim 3, wherein replacing the 2-amino group of the product of step (a) with a 2-chloro group is performed at or less than a temperature of 0° C. and sufficient to carry out the reaction.

5. A method for producing 2-chloro-2'-deoxyadenosine comprising the steps of:

(a) reacting the 6-oxo group of a compound having the formula wherein R is a protecting group selected from the group consisting of acyl and silyl, with reagents selected from the group consisting of (alkyl or fluoroalkyl or cycloalkyl)-sulfonyl, -phosphoryl or -phosphonyl reagents and (aryl or 4-methylbenzene or 2,4,6-triisopropylbenzene)-sulfonyl, -phosphoryl or -phosphonyl reagents to produce a 6-O-(alkyl, substituted alkyl, cycloalkyl, aryl, or substituted aryl)-sulfonyl, -phosphoryl or -phosphonyl group that is capable of hindering nucleophilic attack at the sulphonyl sulfur, phosphoryl or phosphonyl phosphorous and promoting nucleophilic attack at C6 upon subsequent ammonolysis;

(b) reacting the product of step (a) with a halide source and a nitrite source in a solvent compatible with the halide source to replace the 2-amino group with a 2-chloro group;

(c) reacting the product of step (b) with a nitrogen source in a solvent compatible with the nitrogen source to replace the 6-(substituted oxy) leaving group with a 6-amino group; and

(d) reacting the product of step (b) or step (c) with a nitrogen source in a solvent compatible with the nitrogen source to remove the R protecting groups, to produce 2-chloro-2'-deoxyadenosine;

wherein reacting the product of step (a) with a halide source and a nitrite source in a solvent compatible with the halide source to replace the 2-amino group with a 2-chloro group is performed using acetyl chloride and benzyltriethylammonium nitrite.

6. The method according to claim 5, wherein reacting the product of step (a) with a halide source and a nitrite source in a solvent compatible with the halide source to replace the 2-amino group with a 2-chloro group is performed at or less than a temperature of 0° C. and sufficient to carry out the reaction.

7. A method for producing 2-chloro-2'-deoxyadenosine comprising the steps of:

(a) reacting the 6-oxo group of a compound having the formula wherein R is a protecting group selected from the group consisting of acyl and silyl, with a chloride compound selected from the group consisting of metal chlorides, metal chloride salts, acyl chlorides, sulfonyl chlorides, phosphoryl chlorides, silyl chlorides, and alkyl and aryl substituted ammonium chloride salts, to produce a 6-chloro leaving group;

(b) reacting the product of step (a) with a halide source and a nitrite source in a solvent compatible with the halide source to replace the 2-amino group with a 2-chloro group;

(c) reacting the product of step (b) with a nitrogen source in a solvent compatible with the nitrogen source to replace the 6-halo leaving group with a 6-amino group by selective ammonolysis of the 6-leaving group; and (d) reacting the product of steps (b) or (c) with a nitrogen source in a solvent compatible with the nitrogen source to remove the R protecting groups, to produce 2-chloro-2'-deoxyadenosine;

wherein reacting the product of step (a) with a halide source and a nitrite source in a solvent compatible with the halide source to replace the 2-amino group with a 2-chloro group is performed using acetyl chloride and benzyltriethylammonium nitrite.

8. The method according to claim 7, wherein reacting the product of step (a) with a halide source and a nitrite source in a solvent compatible with the halide source to replace the 2-amino group with a 2-chloro group is performed at or less than a temperature of 0° C. and sufficient to carry out the reaction.

9. A method for producing 2-chloro-2'-deoxyadenosine comprising the steps of:
(a) converting the 6-oxo group of a compound having the formula wherein R is a protecting group selected from the group consisting of acetyl and benzoyl, into a 6-leaving group having lesser reactivity than that of the 2-amino group in a diazotization/chloro-dediazoniation displacement reaction selected from the group consisting of alkylsulfonyl, arylsulfonyl, and chloride;

(b) replacing the 2-amino group with a 2-chloro group by diazotization/chloro-dediazoniation of the 2-amino group;

(c) replacing the 6-leaving group with a 6-amino group by selective ammonolysis of the 6-leaving group; and (d) removing the R protecting groups by deacylation, to produce 2-chloro-2'-deoxyadenosine;

wherein replacing the 2-amino group with a 2-chloro group by diazotization/chloro-dediazoniation of the 2-amino group is performed using acetyl chloride and benzyltriethylammonium nitrite.

10. The method according to claim 9, wherein replacing the 2-amino group with a 2-chloro group by diazotization/chloro-dediazoniation of the 2-amino group is performed at or less than a temperature of 0° C. and sufficient to carry out the reaction.

11. A method for producing 2-chloro-2'-deoxyadenosine comprising the steps of:
(a) reacting the 6-oxo group of a compound having the formula wherein R is a protecting group selected from the group consisting of acyl and silyl, with an (alkyl or fluoroalkyl or cycloalkyl)-sulfonyl or -phosphoryl reagent or (aryl or 4-methylbenzene or 2,4,6-triisopropylbenzene)-sulfonyl or -phosphoryl reagent to convert the 6-oxo group to a 6-O-(alkyl, cycloalkyl, or aryl)-sulfonyl or -phosphoryl group;

(b) reacting the product of step (a) with a halide and an organic nitrite in a solvent compatible with the halide to replace the 2-amino group with a 2-chloro group by diazotization/chloro-dediazoniation of the 2-amino group;

(c) reacting the product of step (b) with ammonia in a compatible solvent, or with a nitrogen source capable of being converted to an amino group in a solvent compatible with the nitrogen source, to replace the 6-leaving group with a 6-amino group; and (d) reacting the product of step (c) with a basic reagent in a compatible solvent to remove the R protecting groups by deacylation, to produce 2-chloro-2'-deoxyadenosine;

wherein reacting the product of step (a) with a halide and an organic nitrite in a solvent compatible with the halide to replace the 2-amino group with a 2-chloro group by diazotization/chloro-dediazoniation of the 2-amino group is performed using acetyl chloride and benzyltriethylammonium nitrite.

12. The method according to claim 11, wherein reacting the product of step (a) with a halide and an organic nitrite in a solvent compatible with the halide to replace the 2-amino group with a 2-chloro group by diazotization/chloro-dediazoniation of the 2-amino group is performed at or less than a temperature of 0° C. and sufficient to carry out the reaction.

* * * * *